(12) United States Patent
Grindinger

(10) Patent No.: US 10,518,024 B2
(45) Date of Patent: Dec. 31, 2019

(54) CENTERING APPARATUS

(71) Applicant: Seidenader Maschinenbau GmbH, Markt Schwaben (DE)

(72) Inventor: Herbert Grindinger, Muehldorf/Inn (DE)

(73) Assignee: SEIDENADER MASCHINENBAU GMBH, Markt Schawben (DE)

( * ) Notice: Subject to any disclaimer, the term of this patent is extended or adjusted under 35 U.S.C. 154(b) by 0 days.

(21) Appl. No.: 15/969,433

(22) Filed: May 2, 2018

(65) Prior Publication Data

US 2018/0318494 A1 Nov. 8, 2018

(30) Foreign Application Priority Data

May 2, 2017 (DE) .................. 10 2017 004 233

(51) Int. Cl.
| | | |
|---|---|---|
| *A61M 5/00* | (2006.01) | |
| *A47F 7/00* | (2006.01) | |
| *B65B 39/00* | (2006.01) | |
| *B65G 1/16* | (2006.01) | |
| *B65G 69/00* | (2006.01) | |
| *A61J 1/06* | (2006.01) | |

(52) U.S. Cl.
CPC .......... *A61M 5/002* (2013.01); *A47F 7/0021* (2013.01); *A61M 5/008* (2013.01); *B65B 39/006* (2013.01); *B65B 39/007* (2013.01); *B65G 1/16* (2013.01); *B65G 69/00* (2013.01); *A61J 1/06* (2013.01); *B01L 2200/025* (2013.01); *B65G 2201/0235* (2013.01)

(58) Field of Classification Search
CPC ........ A61M 5/002; A61M 5/008; A61M 5/00; B65G 1/16; B65G 69/00; B65G 2201/0235; A61J 1/06; B65B 39/007; B65B 39/006; B01L 9/06; B01L 9/00; B01L 2200/025; B01L 9/54; A47B 81/00; A47B 87/0223; A47F 7/0028; A47F 7/0021; A47F 7/28; A47F 7/283; A47F 7/0007; A61B 50/22; A61B 50/33; B25H 3/003; B25H 3/04; B25H 3/06
USPC ......... 211/70.6, 70.8, 60.01, 85.18, 74, 70.2, 211/85.13; 206/446, 443
See application file for complete search history.

(56) References Cited

U.S. PATENT DOCUMENTS 712,824 A * 11/1902 Masland .................. A47K 1/09
 211/65
838,473 A * 12/1906 Speiser .................... A47K 1/09
 211/204

(Continued)

FOREIGN PATENT DOCUMENTS

BE 1018901 A4 10/2011
DE 2808042 A1 8/1979

(Continued)

*Primary Examiner* — Jennifer E. Novosad
(74) *Attorney, Agent, or Firm* — McCoy Russell LLP

(57) ABSTRACT

The present disclosure relates to a centering apparatus for the orderly insertion of objects into a storage container comprising: a plate-like base body, a plurality of first indentations adjacent to one another in an outer edge of the base body, a cut-out in the base body, and a plurality of mutually adjacent second indentations in an edge of the cut-out, wherein the first indentations and the second orientations have the same orientation.

17 Claims, 7 Drawing Sheets

(56) References Cited

U.S. PATENT DOCUMENTS

| | | | | |
|---|---|---|---|---|
| 1,717,959 | A * | 6/1929 | Cauffman | A63B 55/00 206/315.6 |
| 2,032,631 | A * | 3/1936 | Pushee | A47F 7/0007 211/49.1 |
| 2,313,905 | A * | 3/1943 | Wallin | A61M 5/008 211/60.1 |
| 2,438,989 | A * | 4/1948 | Billman | B25B 1/2452 131/256 |
| 2,856,067 | A * | 10/1958 | Sparks | B65D 5/5021 206/366 |
| 2,916,159 | A * | 12/1959 | O'Neill | F16B 2/245 206/820 |
| 3,004,673 | A * | 10/1961 | Emery | A47F 7/0028 211/70.8 |
| 3,220,558 | A * | 11/1965 | Olsson | F25D 23/04 211/74 |
| 4,037,766 | A * | 7/1977 | Iacono | B65D 71/50 206/160 |
| 4,142,633 | A * | 3/1979 | Raghavachari | A61M 5/008 141/27 |
| 4,273,416 | A * | 6/1981 | Blum | B01L 9/06 211/73 |
| 4,350,253 | A * | 9/1982 | Rusteberg | B01L 9/06 211/74 |
| 4,961,505 | A * | 10/1990 | Moeller | A47F 7/0035 211/65 |
| 5,267,660 | A * | 12/1993 | Kwon | A63B 55/00 211/70.2 |
| 5,598,924 | A * | 2/1997 | McCann | B25H 3/06 206/372 |
| 5,615,782 | A * | 4/1997 | Choe | A45D 1/00 211/60.1 |
| 5,622,676 | A * | 4/1997 | Lind | B01L 9/543 206/443 |
| 5,678,700 | A * | 10/1997 | Crosson, Jr. | A01K 97/10 211/60.1 |
| 5,843,388 | A * | 12/1998 | Arroyo | A61L 2/26 422/300 |
| 5,992,912 | A * | 11/1999 | Zimm | A45D 29/20 206/1.7 |
| 6,012,595 | A * | 1/2000 | Thilly | A61M 5/008 211/60.1 |
| 6,027,081 | A * | 2/2000 | Rosenberg | A47J 43/287 211/65 |
| 6,041,947 | A * | 3/2000 | Heneveld | A47B 81/005 211/70.1 |
| 6,062,050 | A * | 5/2000 | Lion | A63B 55/00 70/58 |
| 6,216,885 | B1 * | 4/2001 | Guillaume | A61M 5/008 206/366 |
| 6,244,447 | B1 * | 6/2001 | Frieze | A61L 2/07 206/370 |
| 6,375,017 | B1 * | 4/2002 | Schattner | A61M 5/1418 211/70 |
| 6,412,735 | B1 * | 7/2002 | Mathieu | A47K 1/09 211/66 |
| 6,540,072 | B1 * | 4/2003 | Fischer | A61M 5/19 206/366 |
| 6,783,013 | B1 * | 8/2004 | Spann | B25H 3/04 211/60.1 |
| 6,880,709 | B2 * | 4/2005 | Chen | A47B 81/00 211/60.1 |
| 7,025,202 | B2 * | 4/2006 | Jansen | A63B 55/40 206/315.3 |
| 7,175,031 | B2 * | 2/2007 | Matthews | B25H 3/04 211/70.6 |
| 7,503,459 | B2 * | 3/2009 | Grayson | A47B 81/005 211/70.8 |
| 7,721,900 | B2 * | 5/2010 | Waterman | A47B 81/00 211/85.7 |
| D626,743 | S * | 11/2010 | Fairchild | D3/259 |
| 7,857,149 | B2 * | 12/2010 | Cummins | A47B 81/005 211/60.1 |
| 8,028,843 | B2 * | 10/2011 | Guzman | B01L 9/06 211/85.18 |
| 8,069,998 | B2 * | 12/2011 | Thomas | A61L 2/26 211/85.13 |
| 9,084,996 | B2 * | 7/2015 | Chien | B01L 3/5085 |
| 10,072,791 | B2 * | 9/2018 | Beta | F16M 11/28 |
| 2002/0113030 | A1 * | 8/2002 | Belisle | A47B 81/005 211/85.7 |
| 2002/0158032 | A1 * | 10/2002 | Belokin | A47F 5/08 211/71.01 |
| 2003/0000902 | A1 * | 1/2003 | Keis | A47J 47/16 211/89.01 |
| 2008/0255520 | A1 * | 10/2008 | Henderson | A61M 5/19 604/191 |
| 2012/0103861 | A1 * | 5/2012 | Song | A61M 5/002 206/563 |
| 2012/0114457 | A1 | 5/2012 | Nicoletti | |
| 2013/0015151 | A1 * | 1/2013 | Wolfbauer | A01K 97/08 211/70.8 |
| 2014/0034545 | A1 * | 2/2014 | Pawlowski | B65D 25/101 206/565 |
| 2015/0108034 | A1 | 4/2015 | Deutschle et al. | |
| 2017/0183113 | A1 * | 6/2017 | Deutschle | B65B 3/006 |
| 2018/0318494 | A1 * | 11/2018 | Grindinger | A61M 5/002 |

FOREIGN PATENT DOCUMENTS

| | | |
|---|---|---|
| DE | 69715935 T2 | 2/2003 |
| DE | 69333531 T2 | 6/2005 |
| DE | 102006039120 A1 | 3/2008 |
| DE | 202012001250 U1 | 3/2012 |
| DE | 102013111600 A1 | 4/2015 |
| EP | 0790063 A1 | 8/1997 |
| GB | 2014932 A | 9/1979 |

* cited by examiner

CENTERING APPARATUS

CROSS REFERENCE TO RELATED APPLICATIONS

The present application claims priority to German Patent Application No. 10 2017 004 233.0, entitled "CENTERING APPARATUS," and filed on May 2, 2017. The contents of the above-listed application is hereby incorporated by reference in its entirety for all purposes.

TECHNICAL FIELD

The present disclosure relates to a centering apparatus for the orderly insertion of objects into a storage container, also called a nest. The objects to be inserted into the nest or storage container include pharmaceutical containers, for example syringes, ampoules, syringe cartridges, or vials.

BACKGROUND AND SUMMARY

It can occur on the introduction of objects into a storage container that the procedure is impeded due to easily deformed objects (e.g. needle protection) or due to the relatively large tolerances of the storage container. An additional aggravating circumstance is that the objects to be arranged in the storage container have projecting elements (e.g. a finger grip) according to which the diameter to be centered (e.g. syringe barrel) is smaller than the largest diameter at the object (e.g. finger grip).

The typical arrangement of the objects to be arranged in the storage container presents a further problem since rows are often arranged offset from one another. This arrangement requires an exact sideways movement of a centering apparatus.

The disadvantages from the conventional art listed here are overcome with the aid of a centering apparatus according to the following embodiments.

The centering apparatus in accordance with the disclosure for the orderly insertion of objects into a storage container accordingly comprises a plate-like base body, a plurality of first indentations adjacent to one another in an outer edge of the base body, a cut-out in the base body, and a plurality of mutually adjacent second indentations in an edge of the cut-out, wherein the first indentations and the second indentations have the same orientation.

A cut-out here is considered as an opening that extends from the upper side to the lower side of the base body and that has a peripheral marginal region in the base body. The opening is therefore completely surrounded or defined by the base body in its peripheral region.

The objects to be inserted into the storage container can be introduced particularly effectively and fast with the aid of a centering apparatus configured in this manner. It is possible due to the trough-like shape of the indentations in their associated cavities, it is possible to insert objects having a diameter to be centered that is smaller than the largest diameter at the object. This can be done in that the object to be centered is centered with the aid of the indentation and is laterally led away from the object to be centered so that the object arranged in the nest exits the centering apparatus from the open side of the indentation. Provision can be made that the object to be centered partially crosses the indentation of the centering apparatus and, once it is arranged, is led out of an associated indentation by a relative movement. The relative movement is carried out in one direction between the object and the centering apparatus so that the object exits the centering apparatus via the open side of the indentation.

In accordance with an optional modification of the disclosure, the first indentations are arranged along a first straight line and the second indentations are arranged along a second straight line, with the first straight line and the second straight line being in parallel with one another.

An arrangement of the plurality of indentations thereby results that allows a particularly fast filling of a nest.

Provision can additionally be made that the first indentations are arranged offset from the second indentations, optionally by half a width of the indentations. It is thereby possible that rows that are arranged behind one another and that are arranged offset from one another are created by the centering apparatus. The offset of the first indentation with respect to a second indentation here amounts to half the width of the indentations. If the outer edge is in parallel with the edge of the cut-out, the indentations arranged at these two edges are offset from one another in the edge direction.

Provision can optionally be made that the number of first indentations corresponds to the number of second indentations.

In accordance with a further modification of the disclosure, each of the first indentations and each of the second indentations serves the insertion of an object into the storage container. The spacing between the first indentations and the spacing between the second indentations are the same here and are coordinated with the storage container in which the objects to be inserted are arranged.

A plurality of adjacent indentations optionally produce a comb-like arrangement in which the adjacent indentations are separated from one another by a web.

In accordance with a further modification of the disclosure, the outer edge of the base body and the edge of the cut-out are partly or completely slanted in their directions of thickness. In other words, the respective edges are chamfered such that the open sides of the indentations or of the webs arranged between the indentations run out acutely from the indentations.

In accordance with a further development of the disclosure, each of the indentations forms a U shape in their plan views and/or the shape of the first indentations is the same as the shape of the second indentations.

In accordance with a further optional modification of the disclosure, each indentation has a funnel-shaped section from the upper side to a lower side of the base body which tapers from the upper side toward the lower side. The centering of an object to be placed down is thereby produced since the funnel shape compensates deviations with respect to the desired location of the placement.

Provision is made in accordance with a further development that the maximum thickness of an areal region which extends from the outer edge to the edge of the cut-out and which covers the first indentations is smaller than a region of the base body encompassing the second indentations. This is of advantage when two rows of objects have simultaneously been introduced into the storage container by the centering apparatus, with the two rows being arranged behind one another, and a relative movement of the inserted objects takes place into the storage container with respect to the centering apparatus. It is then possible that, due to the smaller thickness or due to the step-like reduction of the thickness at the lower side of the centering apparatus, objects already introduced into the storage container can be moved over without contact, even if only a small spacing increase, or no spacing increase at all, has been made in the vertical direction between the nest and the centering apparatus.

In accordance with a further development of the disclosure, the cut-out has a second edge that is in parallel with the edge provided with the second indentations and likewise extends at a slant in its thickness direction, optionally with the same gradient and orientation as the outer edge and/or the edge of the cut-out provided with the second indentations.

Embodiments of the indentations each have a semicircular section that becomes smaller in diameter from the upper side toward the lower side. An open side of the semicircular section is here arranged in parallel with the edge at which the indentation is provided. Furthermore, each indentation has two webs that project outwardly in a straight line at each of the sides of the open semicircle. The webs are arranged substantially perpendicular to the edge at which the indentation is arranged.

The disclosure furthermore relates to a renester that comprises a centering apparatus in accordance with one of the above-named variants and to a storage container for storing objects, including pharmaceutical containers such as syringes, ampoules, syringe cartridges, or vials.

The centering apparatus is optionally arranged above the storage container and is configured to center the object with respect to an arrangement position in the arrangement container on the insertion of an object into the storage container.

Provision can be made for this purpose that the division of the arrangement positions in the storage container is identical to the division of the plurality of indentations of an edge.

In accordance with a further development of the renester, it comprises a drive unit that is configured to provide a relative movement of the storage container with respect to the centering apparatus. By moving either the storage container and/or the centering apparatus.

Provision can additionally be made that the storage container has a plurality of rows of mutually offset arrangement positions for the objects to be inserted, with a drive unit optionally being provided for carrying out a relative movement between the storage unit and the centering apparatus to move different rows of arrangement positions such that they are aligned with the associated indentations of the centering apparatus.

BRIEF DESCRIPTION OF THE FIGURES

Further features, details and advantages will be explained with reference to the following description of the Figures. There are shown:

FIGS. 1-7 are shown approximately to scale.

DETAILED DESCRIPTION

Figure 1:
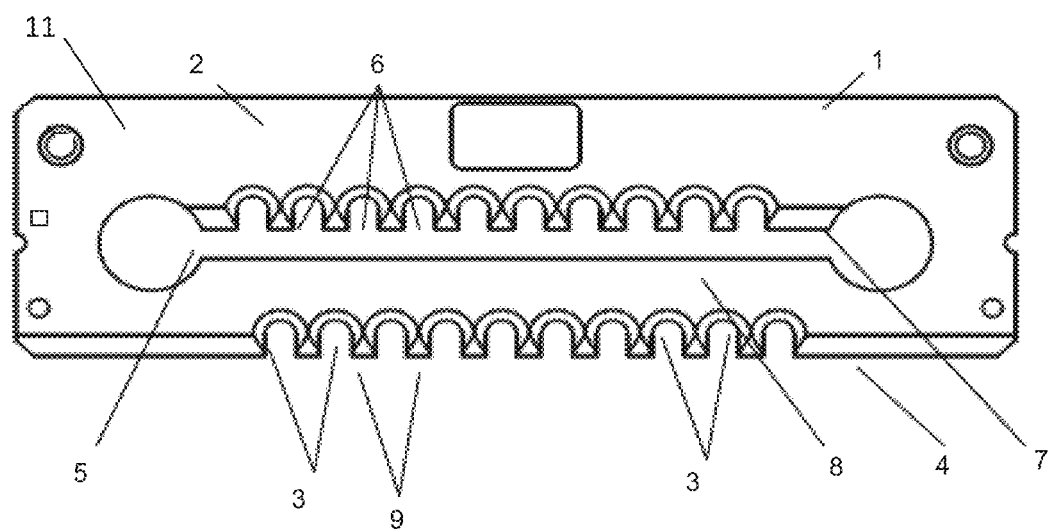
FIG. 1 shows a plan view of the centering apparatus in accordance with the disclosure.

FIG. 1 shows a plan view of an embodiment of an upper side 11 of the centering apparatus 1. The base body 2 has an outer edge 4 here in which a plurality of indentations 3 are provided. The indentations 3 are separated from one another by webs 9. It can further be schematically recognized that the outer edge 4 is slanted in the direction of thickness so that its thickness becomes thinner as the spacing from the base body 2 increases.

The cut-out 5 in the base body 2 that likewise has a first edge 7 is in parallel with the outer edge 4. Second indentations 6 are arranged therein whose shapes substantially correspond to the first indentations 3. In addition, the orientation of the first indentations 3 and of the second indentations 6 is identical. The second indentations 6 are arranged offset with respect to the first indentations 3 in the longitudinal directions of the edges 4, 7. The degree of this offset here amounts to half the width B of an indentation that is likewise measured in the longitudinal direction of the edge.

In addition, the funnel shape of the indentations 3, 6 can be recognized on a view of the upper side 11 of the centering apparatus 1. It is thereby possible to introduce an object into the funnel shape with somewhat less precision and to arrange it with a high positioning accuracy at a predefined location due to the direct deflection of the funnel shape of the indentations 3, 6.

If, for example, a plurality of syringes were picked up by a gripping element, it frequently occurs that a needle protection is not arranged completely orthogonal to the needle arranged therein and the placement in a nest or in an arrangement position of the nest provided for this purpose cannot be performed in a centered manner. Accordingly, without the apparatus 1, a working speed of the gripping element on the transfer of the plurality of syringes to a storage container (e.g. a nest) may be reduced to reliably transfer the syringes to the nest with very high precision.

Such a syringe or such an object furthermore has projecting elements so that a complete passing of the object to be arranged through the indentation is not possible. It is, however, possible to move the centering apparatus with respect to the arranged object such that the object is moved out of the open side of the indentation. This comb-like design of the plurality of indentations arranged in a row considerably simplifies a placement procedure.

To prevent a jamming of objects that do not slide completely into the nest after the movement out of the centering aid, the indentations of the centering aid are chamfered and thus force the objects into their correct positions on a movement.

In addition, the offset arrangement of the two rows of indentations does not require lateral displacement of the centering apparatus on the loading of a nest due to the arrangement positions arranged in an offset manner. A further error source is thereby eliminated which results in a considerable increase in the processing speed.

Figure 2:
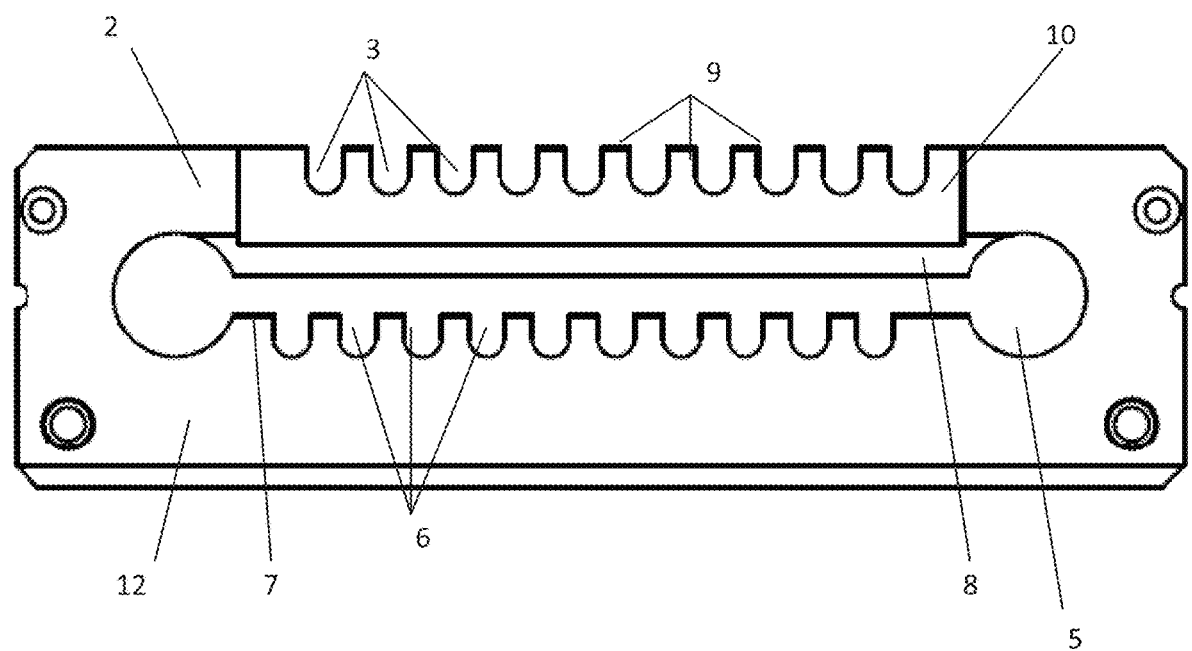
FIG. 2 shows a plan view of the lower side of the centering apparatus in accordance with the disclosure.

FIG. 2 shows the lower side 12 of the centering apparatus 1 and it can be recognized that the second edge 8 of the cut-out 5 also extends obliquely in accordance with the outer edge 4 and the first edge 7 of the cut-out in the thickness direction of the base body 2. On a view from below, it can be recognized that the indentations have a funnel shape so that elements introduced from above can be positioned unerringly in a specific region. The webs 9 that are arranged between the individual indentations and that form a U shape together with the indentations 3, 6 can furthermore also be recognized.

The areal lower side 12 of the base body 2 has a stepped region 10 in the manner of steps that comprises the first indentations 3 from the outer edge 4 up to the second edge 8 of the cut-out 5. This region is stepped in the manner of steps with respect to the other lower side 12 so that the surface of the region 10 optionally has a smaller thickness. The moving over of objects already arranged in a reception container is thereby facilitated that would otherwise possibly bump against the upper side 11.

Figure 3:
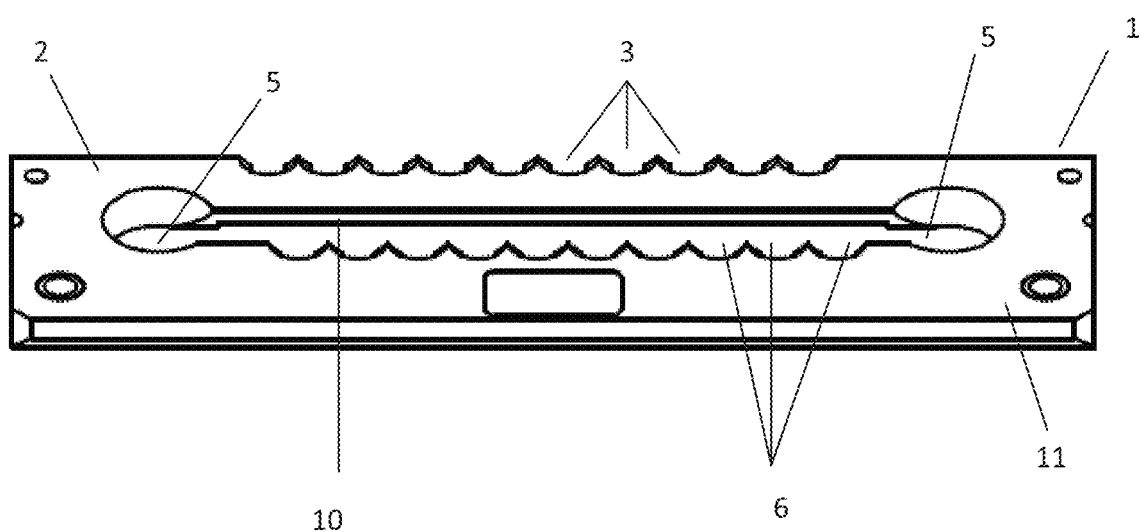
FIG. 3 shows a perspective view of the centering apparatus in accordance with the disclosure.

FIG. 3 is a perspective representation of an embodiment of a centering apparatus 1 in accordance with the disclosure from a rear view. The region 10 can also again be seen here that is characterized by the smaller thickness with respect to the other regions of the centering apparatus 1.

Figure 4:
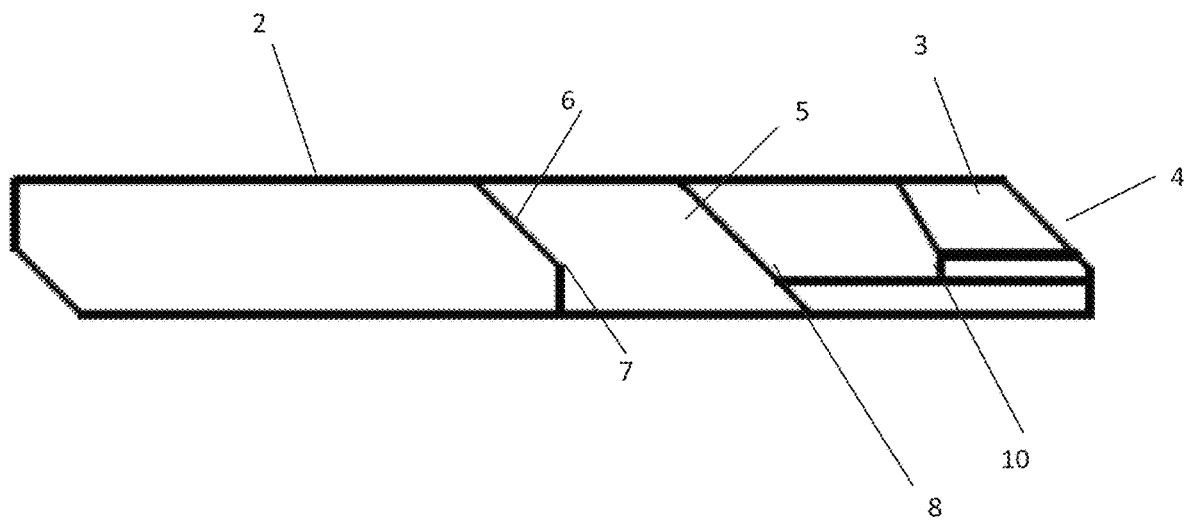
FIG. 4 shows a sectional representation of the centering apparatus.

FIG. 4 shows a sectional representation of an embodiment of a centering apparatus 1 in accordance with the disclosure. The base body 2 and the chamfered edges 7, 8, and 4 can be recognized. The sectional representation provides further understanding of features of the centering apparatus 1 such as the indentations 3, outer edge 4, cut out 5, second indentations 6, first edge 7 and second edge 8.

Figure 5:
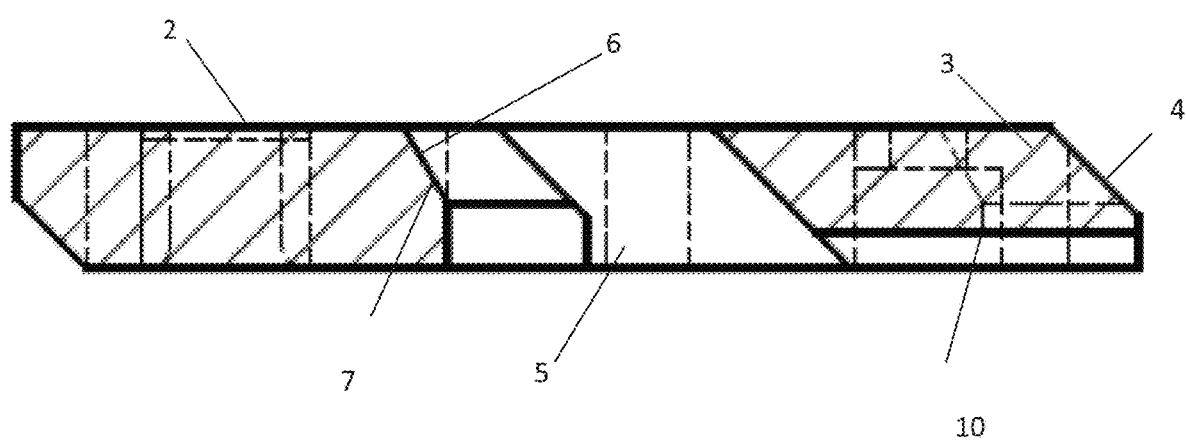
FIG. 5 shows a sectional representation of the centering apparatus in which the elements that are not visible are shown in dashed form.

FIG. 5 shows a further representation of a sectional view of the centering apparatus in accordance with the disclosure in which hidden elements are shown in dashed form. The sectional view provides further understanding of features of the centering apparatus 1 such as the base body 2, indentations 3, outer edge 4, cut out 5, second indentations 6, first edge 7 and second edge 8.

Figure 6:
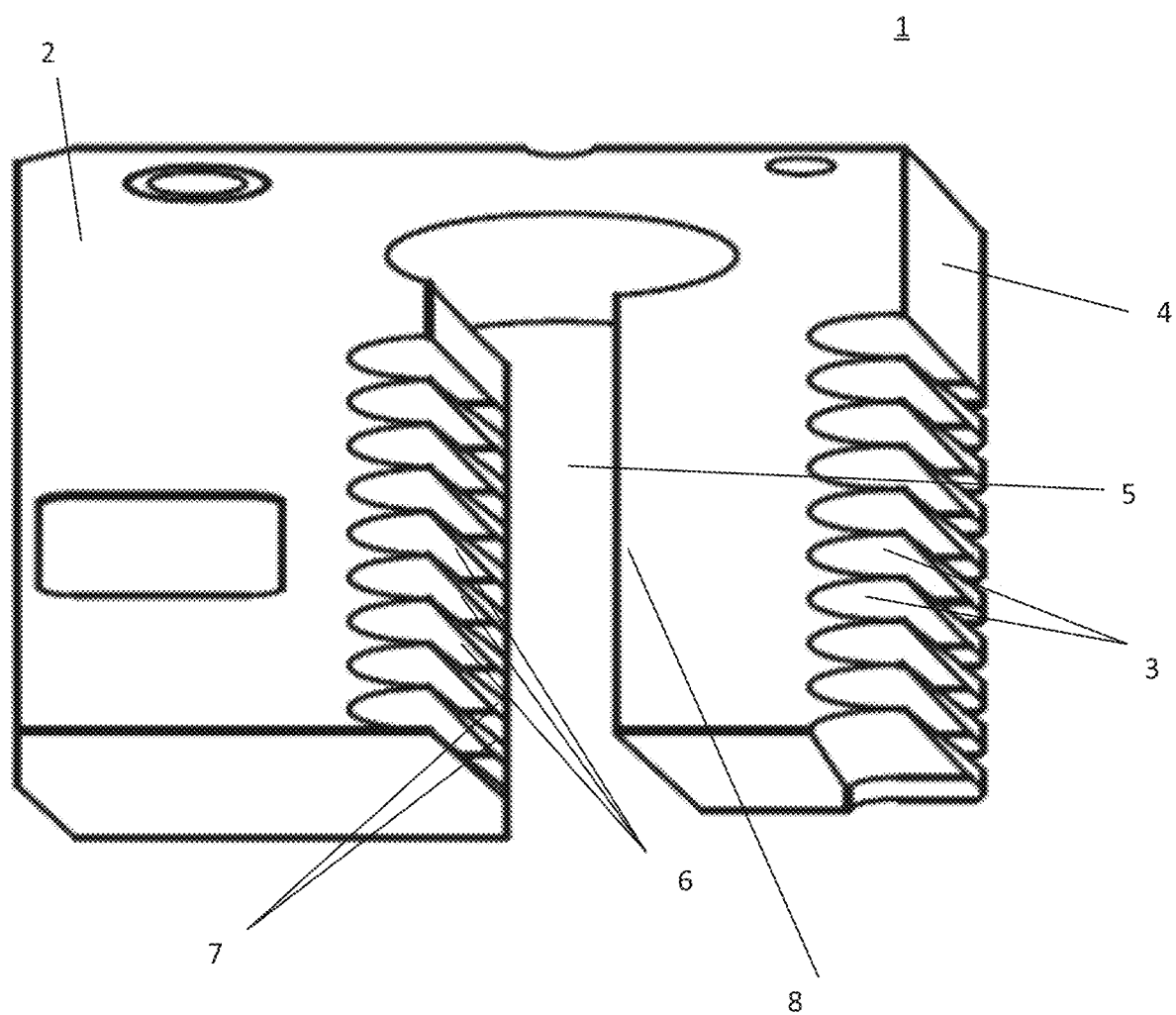
FIG. 6 shows a perspective representation of a sectioned centering apparatus.

FIG. 6 shows a perspective view of the sectional view which is shown in FIG. 5 and with reference to which the design of the base body 2 becomes clear. The perspective view provides further understanding of features of the centering apparatus 1 such as the indentations 3, outer edge 4, cut out 5, second indentations 6, first edge 7 and second edge 8. The tapering funnel shape of the indentations 6 can also be seen in FIG. 6.

Figure 7:
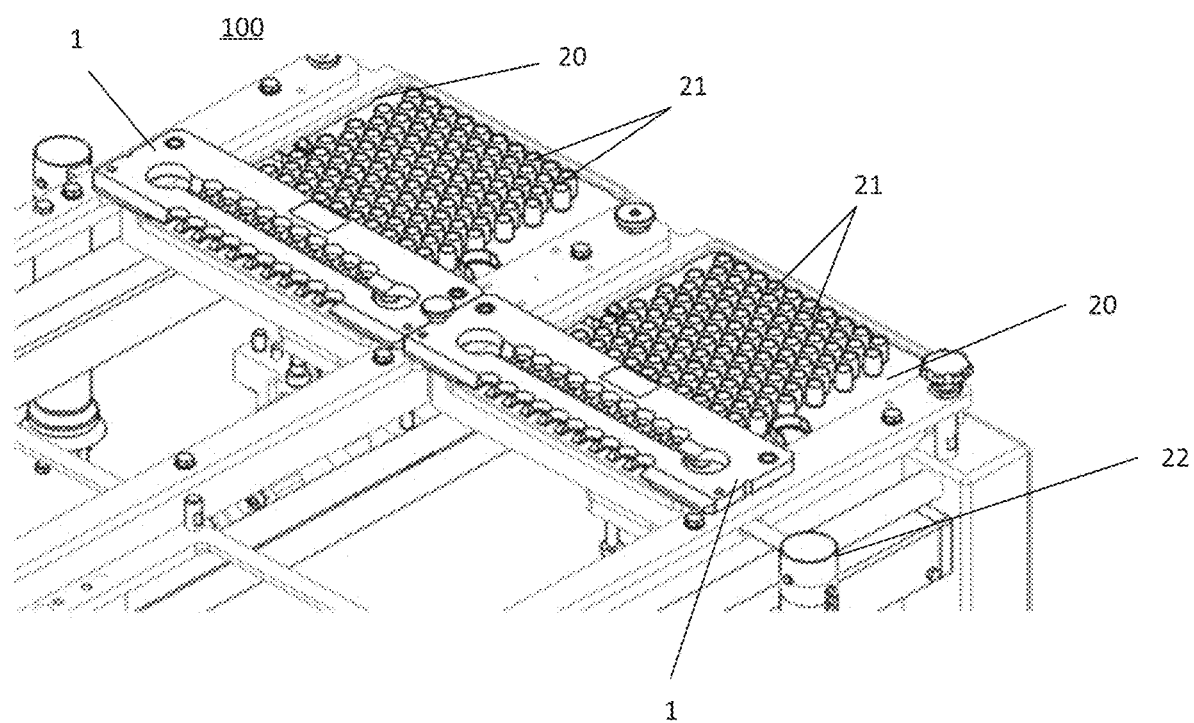
FIG. 7 shows a renester with the centering apparatus in accordance with the disclosure.

FIG. 7 shows a renester that is provided with a centering apparatus 1 in accordance with the disclosure. It can be recognized that the centering apparatus 1 is arranged above a storage container 20 so that the insertion of an object into arrangement positions 21 provided for it is carried out with the aid of an associated indentation 3, 6 of the centering apparatus 1. Once a row is completely filled with the objects, either the centering apparatus 1 or the storage container 20 moves so that the indentations align with still empty arrangement positions 21 subsequent to this movement.

It is thereby possible to allow the arrangement procedure for introducing the objects into the arrangement positions 21 to run faster. This gain in machine speed effects a better machine efficiency overall and produces a smaller energy consumption with an unchanged throughput.

FIGS. 1-7 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. The term approximately is construed to mean plus or minus five percent of the stated values unless otherwise specified. Such claims, whether broader, narrower, equal, or different in scope to the original claims, also are regarded as included within the subject matter of the present disclosure.

The invention claimed is:

1. A centering apparatus for insertion of objects into a storage container comprising:
   a base body including a flat surface;
   a plurality of mutually adjacent first indentations in an outer edge of the base body;
   a cut-out in the base body;
   a plurality of mutually adjacent second indentations in an edge of the cut-out, wherein orientations of the first indentations and the second indentations are the same; and
   a drive unit configured to move the storage container with respect to the centering apparatus;
   wherein the storage container is adapted to have a plurality of rows of mutually offset arrangement positions for the objects;
   wherein the centering apparatus is adapted to be arranged above the storage container and is adapted to center the objects with respect to their arrangement positions in the storage container on the insertion of the objects into the storage container; and
   wherein the drive unit is configured to move different rows of arrangement positions such that they align with the first indentations and the second indentations of the centering apparatus.

2. The apparatus of claim 1, wherein
   the first indentations are arranged along a first straight line;
   the second indentations are arranged along a second straight line; and the first straight line and the second straight line are in parallel with one another.

3. The apparatus of claim 1, wherein the first indentations are arranged offset from the second indentations.

4. The apparatus of claim 1, wherein a number of the first indentations corresponds to a number of the second indentations.

5. The apparatus of claim 1, wherein each of the first indentations and each of the second indentations is adapted to serve the insertion of an object into the storage container.

6. The apparatus of claim 1, wherein the outer edge of the base body and the edge of the cut-out are slanted in respective directions of thickness.

7. The apparatus of claim 1, wherein each of the first indentations and the second indentations produces an arrangement in which adjacent indentations are separated from one another by a web.

8. The apparatus of claim 1, wherein each of the first indentations and the second indentations forms a U shape, and wherein a shape of the first indentations is the same as a shape of the second indentations.

9. The apparatus of claim 1, wherein each of the first indentations and the second indentations has a section from an upper side to a lower side of the base body that extends in a tapering form from the upper side to the lower side.

10. The apparatus of claim 1, wherein a maximum thickness of a region that extends from a second edge of the cut-out to the edge of the cut-out that comprises the second indentations is smaller than a thickness of a region of the base body encompassing the second indentations.

11. The apparatus of claim 10, wherein the second edge of the cut-out is in parallel with the edge of the cut-out provided with the second indentations and the second edge extends in a slanted manner in a direction of thickness.

12. A renester including a centering apparatus configured to insert objects into a storage container, the renester comprising:
a storage container for storing objects; and
the centering apparatus comprising:
a base body including a flat surface;
a plurality of mutually adjacent first indentations in an outer edge of the base body;
a cut-out in the base body;
a plurality of mutually adjacent second indentations in an edge of the cut-out, wherein orientations of the first indentations and the second indentations are the same, and
a drive unit configured to move the storage container with respect to the centering apparatus;
wherein the storage container has a plurality of rows of mutually offset arrangement positions for the objects;
wherein the centering apparatus is arranged above the storage container and serves to center an object with respect to its arrangement position in the storage container on the insertion of the object into the storage container; and
wherein the drive unit moves different rows of arrangement positions such that they align with associated indentations of the centering apparatus.

13. The renester of claim 12, wherein the outer edge of the base body and the edge of the cut-out extend from an upper side of the base body to a side remote from the first indentations toward a lower side of the base body.

14. The renester of claim 12, wherein the cut-out has a second edge that is in parallel with the edge of the cut-out provided with the second indentations with a same gradient and orientation as the outer edge of the base body or the edge of the cut-out provided with the second indentations.

15. The renester of claim 12, wherein the first indentations are arranged offset from the second indentations by half a width of the first indentations.

16. The renester of claim 12, wherein the storage container is adapted to store one of syringes, ampules, syringe cartridges, or vials.

17. The renester of claim 12, wherein the drive unit is provided for carrying out a relative movement between the storage container and the centering apparatus.

* * * * *